United States Patent
Cordova et al.

(10) Patent No.: US 7,585,900 B2
(45) Date of Patent: Sep. 8, 2009

(54) LOW-TACK OPHTHALMIC AND OTORHINOLARYNGOLOGICAL DEVICE MATERIALS

(75) Inventors: Diana M. Cordova, Duncanville, TX (US); Mutlu Karakelle, Fort Worth, TX (US); Chance Lehman, Dallas, TX (US); Douglas C. Schlueter, Azle, TX (US); Joseph I. Weinschenk, III, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/780,649

(22) Filed: Jul. 20, 2007

(65) Prior Publication Data

US 2008/0021129 A1 Jan. 24, 2008

Related U.S. Application Data

(60) Provisional application No. 60/832,478, filed on Jul. 21, 2006.

(51) Int. Cl.
*C08F 290/06* (2006.01)
*G02B 1/04* (2006.01)
*G02C 7/04* (2006.01)
*A61F 2/14* (2006.01)
*A61F 2/16* (2006.01)
*C08F 18/02* (2006.01)
*C08F 22/10* (2006.01)
*C08F 18/16* (2006.01)
*C08F 20/18* (2006.01)
*C08F 220/30* (2006.01)

(52) U.S. Cl. .................. 523/107; 523/106; 351/160 R; 623/6.11; 623/6.59; 526/279; 526/319; 526/321; 526/326; 526/323.1; 526/323.2

(58) Field of Classification Search ................ 523/106, 523/107; 526/259, 279, 319, 321, 326, 323.1, 526/323.2; 623/6.11, 6.59; 351/160 R
See application file for complete search history.

(56) References Cited

U.S. PATENT DOCUMENTS

| | | | |
|---|---|---|---|
| 3,842,059 A | 10/1974 | Milkovich et al. ......... 260/93.5 |
| 3,862,077 A | 1/1975 | Schulz et al. .............. 260/29.6 |
| 4,528,311 A * | 7/1985 | Beard et al. .................... 524/91 |
| 4,834,750 A | 5/1989 | Gupta ........................... 623/6 |
| 5,290,892 A | 3/1994 | Namdaran et al. .......... 526/259 |
| 5,331,073 A | 7/1994 | Weinschenk, III et al. .. 526/264 |
| 5,359,021 A | 10/1994 | Weinschenk, III et al. .. 526/264 |
| 5,470,932 A | 11/1995 | Jinkerson .................... 526/312 |
| 5,603,774 A | 2/1997 | LeBoeuf et al. ................ 134/1 |
| 5,693,095 A | 12/1997 | Freeman et al. ................ 623/6 |
| 5,882,421 A | 3/1999 | LeBoeuf et al. ................ 134/1 |
| 6,245,106 B1 | 6/2001 | Makker et al. ............. 623/5.16 |
| 6,528,602 B1 | 3/2003 | Freeman et al. ............. 526/259 |
| 6,653,422 B2 | 11/2003 | Freeman et al. ............. 526/259 |
| 6,703,466 B1 | 3/2004 | Karakelle et al. ........... 526/259 |
| 6,713,583 B2 | 3/2004 | Liao et al. ................... 526/319 |
| 6,723,816 B2 | 4/2004 | Salamone et al. ............. 528/32 |
| 6,730,767 B2 | 5/2004 | Salamone et al. ............. 528/43 |
| 6,762,271 B2 | 7/2004 | Salamone et al. ............. 528/43 |
| 6,806,337 B2 | 10/2004 | Schlueter et al. ........ 526/318.43 |
| 6,822,016 B2 * | 11/2004 | McCabe et al. ............. 523/107 |
| 6,861,065 B2 | 3/2005 | Hodd et al. .................. 424/427 |
| 6,872,793 B1 | 3/2005 | Schlueter .................... 526/326 |
| 6,906,162 B2 * | 6/2005 | Salamone et al. ............. 528/43 |
| RE38,935 E | 1/2006 | Makker et al. ............. 623/5.16 |
| 2006/0281888 A1 | 12/2006 | Schlueter ............... 526/318.44 |
| 2006/0282163 A1 | 12/2006 | Schlueter et al. ........... 623/6.11 |

FOREIGN PATENT DOCUMENTS

| | | |
|---|---|---|
| EP | 0657751 A2 | 6/1995 |
| WO | WO 01/18079 A1 | 3/2001 |
| WO | WO 2005/109041 A1 | 11/2005 |
| WO | WO2007100979 A3 | 9/2007 |

* cited by examiner

*Primary Examiner*—Mark Eashoo
*Assistant Examiner*—Michael Pepitone
(74) *Attorney, Agent, or Firm*—Patrick M. Ryan

(57) ABSTRACT

Disclosed are soft, high refractive index, acrylic materials. These materials, especially useful as intraocular lens materials, contain an aryl acrylic hydrophobic monomer as the single principal device-forming monomer and a tack-reducing macromer additive. In addition to their use as intraocular lens materials, the present materials are also suitable for use in other ophthalmic or otorhinolaryngological devices, such as contact lenses, keratoprostheses, corneal inlays or rings; otological ventilation tubes and nasal implants.

17 Claims, No Drawings

LOW-TACK OPHTHALMIC AND OTORHINOLARYNGOLOGICAL DEVICE MATERIALS

This application claims priority to U.S. Provisional Application, U.S. Ser. No. 60/832,478 filed Jul. 21, 2006.

FIELD OF INVENTION

This invention is directed to acrylic device materials. In particular, this invention relates to low-tack, high refractive index acrylic device materials particularly suited for use as intraocular lens ("IOL") materials.

BACKGROUND OF INVENTION

With the recent advances in small-incision cataract surgery, increased emphasis has been placed on developing soft, foldable materials suitable for use in artificial lenses. In general, these materials fall into one of three categories: hydrogels, silicones, and acrylics.

In general, hydrogel materials have a relatively low refractive index, making them less desirable than other materials because of the thicker lens optic necessary to achieve a given refractive power. Silicone materials generally have a higher refractive index than hydrogels, but tend to unfold explosively after being placed in the eye in a folded position. Explosive unfolding can potentially damage the corneal endothelium and/or rupture the natural lens capsule. Acrylic materials are desirable because they typically have a higher refractive index than silicone materials and unfold more slowly or controllably than silicone materials.

U.S. Pat. No. 5,290,892 discloses high refractive index, acrylic materials suitable for use as an IOL material. These acrylic materials contain, as principal components, two aryl acrylic monomers. They also contain a cross-linking component. The IOLs made of these acrylic materials can be rolled or folded for insertion through small incisions.

U.S. Pat. No. 5,331,073 also discloses soft acrylic IOL materials. These materials contain as principal components, two acrylic monomers which are defined by the properties of their respective homopolymers. The first monomer is defined as one in which its homopolymer has a refractive index of at least about 1.50. The second monomer is defined as one in which its homopolymer has a glass transition temperature less than about 22° C. These IOL materials also contain a cross-linking component. Additionally, these materials may optionally contain a fourth constituent, different from the first three constituents, which is derived from a hydrophilic monomer. These materials preferably have a total of less than about 15% by weight of a hydrophilic component.

U.S. Pat. No. 5,693,095 discloses foldable ophthalmic lens materials comprising a total of at least 90% by weight of only two principal lens-forming monomers. One lens-forming monomer is an aryl acrylic hydrophobic monomer. The other lens-forming monomer is a hydrophilic monomer. The lens materials also comprise a cross-linking monomer and optionally comprise a UV absorber, polymerization initiators, reactive UV absorbers and reactive blue-light absorbers.

U.S. Pat. No. 6,653,422 discloses foldable ophthalmic lens materials consisting essentially of a single device-forming monomer and at least one cross-linking monomer. The materials optionally contain a reactive UV absorber and optionally contain a reactive blue-light absorber. The single device-forming monomer is present in an amount of at least about 80% by weight. The device-forming monomer is an aryl acrylic hydrophobic monomer.

Some foldable acrylic materials are tacky. Foldable ophthalmic lenses made of tacky acrylic materials are difficult to handle. Attempts have been made to reduce tackiness so that the lenses are easier to process or handle, easier to fold or deform, and have shorter unfolding times. For example, U.S. Pat. No. 6,713,583 discloses ophthalmic lenses made of a material that includes branched chain alkyl groups in an amount effective to reduce tackiness. U.S. Pat. No. 4,834,750 discloses intraocular lenses made from materials that optionally include a fluoroacrylate component to reduce surface tackiness. U.S. Pat. No. 5,331,073 discloses acrylic materials that optionally include a hydrophilic component that is present in an amount sufficient to reduce the materials' tackiness. U.S. Pat. No. 5,603,774 discloses a plasma treatment process for reducing the tackiness of a soft acrylic article.

SUMMARY OF THE INVENTION

Improved soft, foldable acrylic materials which are particularly suited for use as IOLs, but which are also useful as other ophthalmic or otorhinoloaryngological devices, such as contact lenses, keratoprostheses, corneal rings or inlays, otological ventilation tubes and nasal implants have now been discovered. These materials contain only one principal lens-forming component, an aryl acrylic hydrophobic monomer, in an amount of at least about 75% by weight. The materials also contain a macromer additive in an amount sufficient to reduce the materials' tackiness. The macromer additive is a dimethylacryloxypropyl-terminated polydimethylsiloxane macromer. The remainder of the material comprises a cross-linking monomer and optionally one or more additional components selected from the group consisting of UV-light absorbing compounds and blue-light absorbing compounds.

DETAILED DESCRIPTION OF THE INVENTION

The ophthalmic or otorhinolaryngological device materials of the present invention comprise only one principal device-forming monomer. For convenience, the device-forming monomer may be referred to as a lens-forming monomer, particularly with reference to an IOL. The materials of the present invention, however, are also suitable for use as other ophthalmic or otorhinolaryngological devices such as contact lenses, keratoprostheses, corneal inlays or rings, otological ventilation tubes and nasal implants.

The aryl acrylic hydrophobic monomers suitable for use as the principal lens-forming monomer in the materials of the present invention have the formula

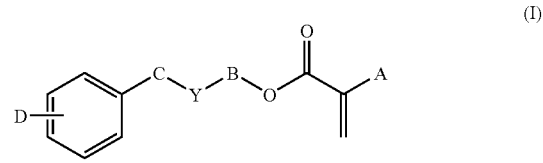

(I)

wherein:
A is H, $CH_3$, $CH_2CH_3$, or $CH_2OH$;
B is $(CH_2)_m$ or $[O(CH_2)_2]_n$;
C is $(CH_2)_w$;
m is 2-6;
n is 1-10;
Y is nothing, O, S, or NR, provided that if Y is O, S, or NR, then B is $(CH_2)_m$;

R is H, $CH_3$, $C_nH_{2n+1}$ (n=1-10), iso-$OC_3H_7$, $C_6H_5$, or $CH_2C_6H_5$;

w is 0-6, provided that m+w≦8; and

D is H, $C_1$-$C_4$ alkyl, $C_1$-$C_4$ alkoxy, $C_6H_5$, $CH_2C_6H_5$ or halogen.

Preferred aryl acrylic hydrophobic monomers for use in the materials of the present invention are those wherein A is $CH_3$, B is $(CH_2)_m$, m is 2-5, Y is nothing or O, w is 0-1, and D is H. Most preferred are 4-phenylbutyl methacrylate, 5-phenylpentyl methacrylate, 2-benzyloxyethyl methacrylate, and 3-benzyloxypropyl methacrylate.

Monomers of structure I can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

The materials of the present invention comprise a total of at least about 75%, preferably at least about 80%, by weight or more of the principal lens-forming monomer.

In addition to the principal lens-forming monomer, the materials of the present invention contain a macromer additive in an amount sufficient to reduce the material's tackiness. Generally, the amount of macromer additive in the materials of the present invention will range from 0.5-3.9% (w/w), and preferably will range from 0.5-2% (w/w), most preferably 0.8-1.2% (w/w). The macromer is a dimethylacryloxypropyl-terminated polydimethylsiloxane macromer of the formula:

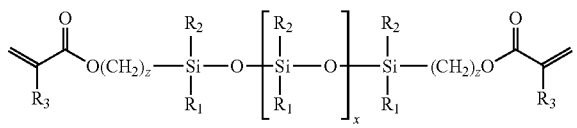

wherein $R_1$ and $R_2$ are independently —$CH_3$, —$CH_2CH_3$, —$CH_2CH_2CH_2CH_3$, $CH_2CH_2CH_2CH_3$, —$C_6H_5$, —$CH_2C_6H_5$, —$CH_2CH_2C_6H_5$, —$CH_2CH_2CH_2C_6H_5$, or —$CH_2CH_2CH_2CH_2C_6H_5$;

$R_3$ is H, $CH_3$, or $CH_2CH_3$;

z is 2-11; and x indicates the number of repeating units and determines the molecular weight of the macromer.

Preferred macromers are those wherein $R_1$=$R_2$=$CH_3$;

$R_3$ is H, $CH_3$, or $CH_2CH_3$; and z=3; and x=0-43.

More preferred macromers are those wherein $R_1$, $R_2$, $R_3$, and z are as defined above for the preferred macromers and x is 0-22. In one embodiment, x is 5-14 (generally corresponding to a macromer molecular weight ($M_n$) of 800-1400). In another embodiment, x is 2-5 (generally corresponding to a macromer molecular weight ($M_n$) of 550-700).

Dimethylacryloxypropyl-terminated polydimethylsiloxanes of the above formula ("PDMS"), also known as methacryloxypropyl terminated polydimethyl siloxanes, can be made by known methods. Some PDMS compounds are commercially available from Gelest, Inc. in molecular weights ($M_n$) ranging from 800-1400 (mid-range $M_n$ estimated as 1000). There are higher ($M_n$ 4K-6K, 5K-20K, 20K -30K) and lower ($M_n$ 386, 550-700) molecular weight grades of dimethacryloxypropyl-terminated siloxane commercially available. The macromer additive selection is limited by solubility (in the remainder of the copolymer material formulation) and formulation clarity (the copolymer material should be clear). Generally, PDMS used in the present invention will have a molecular weight ($M_n$) of about 300-about 3500 and preferably about 350-about 2000. In one embodiment, an especially preferred PDMS has a $M_n$ from about 800-about 1400. In another embodiment, an especially preferred PDMS has a $M_n$ from about 550-about 700.

The copolymer materials of the present invention are cross-linked. The copolymerizable cross-linking agent used in the copolymers of this invention may be any terminally ethylenically unsaturated compound having more than one unsaturated group. Suitable cross-linking agents include, for example: ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C$(=O)O—$(CH_2CH_2O)_p$—$C$(=O)$C(CH_3)$=$CH_2$ where p=1-50; and $CH_2$=$C(CH_3)C$(=O)$O(CH_2)_t$O—$C$(=O)$C(CH_3)$=$CH_2$ where t=3-20; and their corresponding acrylates. A preferred cross-linking monomer is $CH_2$=$C(CH_3)C$(=O)O—$(CH_2CH_2O)_p$—$C$(=O)$C(CH_3)$=$CH_2$ where p is such that the number-average molecular weight is about 400, about 600, or about 1000. The most preferred cross-linking agent is $CH_2$=$C(CH_3)C$(=O)O—$(CH_2CH_2O)_p$—$C$(=O)$C(CH_3)$=$CH_2$ where p is such that the number-average molecular weight is about 1000 ("PEG (1000)DMA").

The chosen cross-linking agent should be soluble in the chosen monomer of structure I to minimize curing problems. When p approaches the upper end of the range of 1-50, the $CH_2$=$C(CH_3)C$(=O)O—$(CH_2CH_2O)_p$—$C$(=O)$C(CH_3)$=$CH_2$ cross-linker may not be soluble at desired levels in some monomers of structure I, even with the aid of heat or sonication.

Generally, only one cross-linking monomer will be present in the device materials of the present invention. In some cases, however, combinations of cross-linking monomers may be desirable. A preferred combination of cross-linking monomers is PEG(1000)DMA and ethylene glycol dimethacrylate ("EGDMA").

Generally, the total amount of the cross-linking component is at least 0.1% by weight and, depending on the identity and concentration of the remaining components and the desired physical properties, can range to about 20% by weight. The preferred concentration range for the cross-linking component is 0.1-17% (w/w).

In addition to the aryl acrylic hydrophobic lens-forming monomer, the macromer additive, and the cross-linking component, the lens material of the present invention may also contain a total of up to about 10% by weight of additional components which serve other purposes, such as reactive UV and/or blue-light absorbers.

Preferred reactive UV absorbers are 2-(2'-hydroxy-3'-methallyl-5'-methylphenyl)benzotriazole, commercially available as o-Methallyl Tinuvin P ("oMTP") from Polysciences, Inc., Warrington, Pa., and 2-[3-(2H-benzotriazol-2-yl)-4-hydroxyphenylethyl]methacrylate ("BHMA"). UV absorbers are typically present in an amount from about 0.1-5% (w/w).

Suitable reactive blue-light absorbing compounds are those described in U.S. Pat. No. 5,470,932, the entire contents of which are hereby incorporated by reference. Blue-light absorbers are typically present in an amount from about 0.01-0.5% (w/w).

Suitable polymerization initiators include thermal initiators and photoinitiators. Preferred thermal initiators include peroxy free-radical initiators, such as t-butyl (peroxy-2-ethyl) hexanoate and di-(tert-butylcyclohexyl) peroxydicarbonate (commercially available as Perkadoxe® 16 from Akzo Chemicals Inc., Chicago, Ill.). Particularly in cases where the lens material does not contain a blue-light absorbing chromophore, preferred photoinitiators include benzoylphosphine oxide photoinitiators, such as the blue-light initiator 2,4,6-trimethyl-benzoyidiphenylphosphine oxide, commercially available as Lucirin® TPO from BASF Corporation (Charlotte, N.C.). Initiators are typically present in an amount of about 5% (w/w) or less. Because free-radical initiators do not become chemically a part of the polymers formed, the total amount of initiator is customarily not included when determining the amounts of other ingredients.

The identity and amount of the principal lens-forming monomer described above and the identity and amount of any additional components are determined by the desired properties of the finished ophthalmic lens. Preferably, the ingredients and their proportion are selected so that the acrylic lens materials of the present invention possess the following properties, which make the materials of the present invention particularly suitable for use in IOLs which are to be inserted through incisions of 5 mm or less.

The lens material preferably has a refractive index in the dry state of at least about 1.50 as measured by an Abbe' refractometer at 589 nm (Na light source). For a given optic diameter, optics made from materials having a refractive index lower than 1.50 are necessarily thicker than optics of the same power which are made from materials having a higher refractive index. As such, IOL optics made from materials having a refractive index lower than about 1.50 generally require relatively larger incisions for IOL implantation.

The glass-transition temperature ("Tg") of the lens material, which affects the material's folding and unfolding characteristics, is preferably below about 25° C., and more preferably below about 15° C. Tg is measured by differential scanning calorimetry at 10° C./min., and is determined as the half-height of the heat capacity increase.

The lens material will have an elongation (strain at break) of at least 75%, preferably at least 90%, and most preferably at least 100%. This property indicates that the lens generally will not crack, tear or split when folded. Elongation of polymer samples is determined on dumbbell shaped tension test specimens with a 20 mm total length, length in the grip area of 11 mm, overall width of 2.49 mm, 0.833 mm width of the narrow section, a fillet radius of 8.83 mm, and a thickness of 0.9 mm. Testing is performed on samples at standard laboratory conditions of 23±2° C. and 50±5% relative humidity using a tensile tester. The grip distance is set at 11 mm and a crosshead speed is set at 500 mm/minute and the sample is pulled to failure. The strain at break is reported as a fraction of the displacement at failure to the original grip distance. Stress at break is calculated at the maximum load for the sample, typically the load when the sample breaks, assuming that the initial area remains constant. The Young's modulus is calculated from the instantaneous slope of the stress-strain curve in the linear elastic region. The 25% secant modulus is calculated as the slope of a straight line drawn on the stress-strain curve between 0% strain and 25% strain. The 100% secant modulus is calculated as the slope of a straight line drawn on the stress-strain curve between 0% strain and 100% strain.

IOLs constructed of the materials of the present invention can be of any design capable of being rolled or folded into a small cross section that can fit through a relatively smaller incision. For example, the IOLs can be of what is known as a one piece or multipiece design, and comprise optic and haptic components. The optic is that portion which serves as the lens. The haptics are attached to the optic and hold the optic in its proper place in the eye. The optic and haptic(s) can be of the same or different material. A multipiece lens is so called because the optic and the haptic(s) are made separately and then the haptics are attached to the optic. In a single piece lens, the optic and the haptics are formed out of one piece of material. Depending on the material, the haptics are then cut, or lathed, out of the material to produce the IOL.

The invention will be further illustrated by the following examples, which are intended to be illustrative, but not limiting.

EXAMPLE 1

Synthesis of 4-phenylbutyl methacrylate ("PBMA")

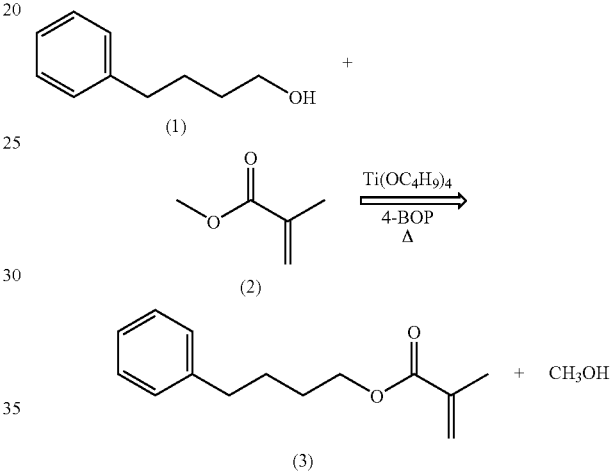

A three neck round bottom flask containing a teflon coated magnetic stirring bar was successively charged with 120 mL (1.09 mol) of methyl methacrylate (2), 5.35 g (0.015 mol) of titanium tetrabutoxide (Ti(OC$_4$H$_9$)$_4$), 60 mL (0.39 mol) of 4-phenyl-1-butanol (1), and 14.6 g (0.073 mol) of 4-benzyloxyphenol (4-BOP). An addition funnel, thermometer, and a short path still head with thermometer and receiver flask were placed in the flask necks. The flask was placed in an oil bath and the temperature was increased until distillation began. Methyl methacrylate (2) was placed in the addition funnel and was added dropwise at the same rate as the distillate. The reaction mixture was heated for 4 hours and then cooled to room temperature. The crude product was vacuum distilled to isolate 62.8 g (0.29 mol, 74%) of 4-phenylbutyl methacrylate (3) as a clear, colorless liquid.

EXAMPLE 2

Synthesis of 3-benzyloxypropyl methacrylate

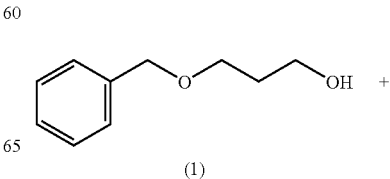

-continued

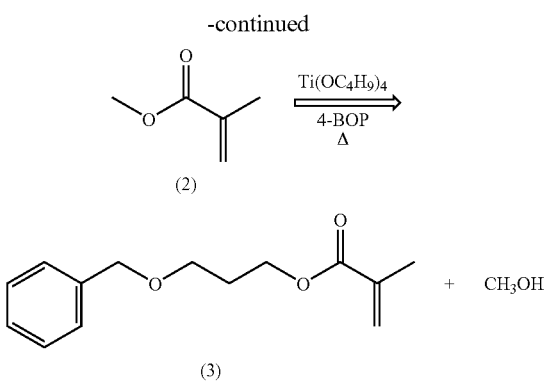

A three neck round bottom flask containing a teflon coated magnetic stirring bar was successively charged with 95 mL (0.884 mol) of methyl methacrylate (2), 4.22 g (0.012 mol) of titanium tetrabutoxide (Ti(OC$_4$H$_9$)$_4$), 50 mL (0.316 mol) of 3-benzyloxy-1-propanol (1), and 14.6 g (0.073 mol) of 4-benzyloxyphenol (4-BOP). An addition funnel, thermometer, and a short path still head with thermometer and receiver flask were placed in the flask necks. The flask was placed in an oil bath and the temperature was increased until distillation began. Methyl methacrylate (2) was placed in the addition funnel and was added dropwise at the same rate as the distillate. The reaction mixture was heated for 4 hours and then cooled to room temperature. The crude product was vacuum distilled to isolate 36.5 g (0.156 mol, 49%) of 3-benzyloxypropyl methacrylate (3) as a clear, colorless liquid.

EXAMPLE 3

Preferred Intraocular Lens Material

A preferred intraocular lens material is presented below. All amounts are expressed as % by weight. This formulation can be initiated with a peroxy free-radical initiator, such as 1% di-(4-t-butylcyclohexyl)peroxydicarbonate ("PERK16S")

| Ingredient | % (w/w) |
| --- | --- |
| PBMA | 82-84 |
| PDMS (MW = 800-1400) | 0.5-2 |
| PEG(1000)DMA | 13-15 |
| EGDMA | 1 |
| UV absorber | 0.1-5 |
| Blue-light absorber | 0.01-0.5 |

The chemicals are weighed, mixed, and filtered together. The resulting formulation solution is flushed with nitrogen gas and then transferred to a glovebox with a low oxygen atmosphere. The formulation is pipetted into degassed polypropylene molds. The assembled molds are then transferred to an oven and cured at 90° C. for 1 hour, followed by a post-cure at 110° C. for 1 hour. The polymer samples are removed from the molds after cooling. The low tack property of the samples is noticeable at this step of the preparation. The samples are extracted with acetone and vacuum dried. Subsequent tack evaluations show the materials are less tacky than control samples not containing PDMS.

EXAMPLES 4-10

Each of the formulations of Examples 4-10 was prepared as follows. In each case, the "PDMS" was dimethylacryloxypropyl-terminated polydimethylsiloxane (R$_1$=R$_2$=R$_3$=CH$_3$, and z=3).

Monomers were weighed into amber glass scintillation vials with teflon-lined screw-caps. The vials are shaken 1 hr on an orbital shaker until the liquid PDMS formed a uniform, clear solution. Then the initiator was added to the sample in an amount equal to about 1% of the total formulation weight. The initiator for each sample was PERK16S. After filtering the sample through a 1-micron glass fiber membrane syringe filter connected to a 5-mL latex-free, oil-free syringe, the formulation was purged with nitrogen for 5-15 min and then capped to keep out air. Samples were cast into polypropylene slab or lens molds in a glovebox (a containment device which provides a microenvironment of a dry nitrogen atmosphere with less than 50-140 ppm oxygen). To maintain the mold geometry during curing, spring clamps are used on the slab molds. The slab and lens molds were previously prepared by heating at 90° C. for more than 2 hrs. under vacuum (less than 0.1 in Hg pressure), then transferring the molds to the glovebox. After filling the molds, the samples were transferred from the glove box to a curing oven and heated for 1 hr. at 90° C., followed by 1 hr. at 110° C. The samples were cooled to room temperature and then stored briefly in the freezer before opening the molds. After opening the molds, the cured samples were extracted in acetone to remove any materials not bound to the cross-linked network and then dried in air. Finally, the samples were placed into polypropylene tissue capsules and then into a vacuum oven and dried under vacuum at 60-63° C. and below 0.1 inches Hg pressure. The samples were inspected visually to record whether they were clear.

Physical property data labeled "Stress at Break, "Strain at Break", "Young's Modulus," "25% Secant Modulus," and "100% Secant Modulus" in the tables below was assessed according to the methods referred to above. "Quantitative Tack" was determined by the following method. The tack testing apparatus has two parts: a bottom component attached to the lower stationary Instron grip and a top component attached to the upper movable Instron grip. At the center of the bottom component is a 4-mm diameter cylindrical stainless steel stage attached on its end and thus standing vertical. Testing specimens are placed on the exposed end of the stage which is finely polished to mimic the finish on most stainless steel surgical instruments. The top component contains a 4.1-mm diameter circular opening that slides over the cylindrical stage as the top component is lowered. During testing, the upper component is raised and the edges of the circular opening contact the specimen and detach it from the cylindrical stage. In preparation for testing, the tack testing apparatus is mechanically fixed to an Instron testing instrument. Test specimens are prepared by punching 6-mm disks out of polymer slabs with a die. Prior to each experimental run, the upper component of the apparatus is lowered so it is just below the top of the 5-mm diameter polished stainless steel cylindrical stage at the center of the base. It is important to verify that no part of the upper component in any way contacts the cylinder. If any contact occurs, it will register a load during testing due to frictional forces and negatively impact the quality of the results. Once the top is set in place, a polymer disk is placed on the stage, and a 50-g weight is then placed on the disk. After a one-minute equilibration time, the run is started. The testing method simply consists of raising the upper component of the apparatus at a constant rate of 10 mm/min until the disk is fully separated from the cylinder. To maintain a clean and consistent contact surface, the lower stage is cleaned with acetone and allowed to fully dry between samples. A load-displacement curve is generated for each run. This curve is used for calculating the energy ("Tack: Total Energy") required to detach the sample from the cylinder. Detachment energy is determined by calculating the area under the load-displacement curve. Qualitative observations were obtained by handling the samples with metal forceps ("Tackiness by Handling").

Unless indicated otherwise, all ingredient amounts shown below are listed as % (w/w). The following abbreviations are used in Tables 1-4:
PBMA: 4-phenylbutylmethacrylate
PDMS: dimethacryloxypropyl-terminated polydimethylsiloxane
PEG(1000)DMA: polyethylene glycol 1000 dimethacrylate
EGDMA: ethylene glycoldimethacrylate
BHMA: 2-[3-(2H-benzotriazol-2-yl)-4-hydroxyphenylethyl]methacrylate.

TABLE 1

| INGREDIENT | CONTROL | EX. 4 |
|---|---|---|
| PBMA | 83.99 | 83.98 |
| PDMS (MW = 800-1400) | — | 2.01 |
| PEG(1000) DMA | 15.00 | 12.99 |
| EGDMA | 1.01 | 1.02 |
| Tack: Total Energy (mJ) | 2.01 ± 0.24 | 0.62 ± 0.23 |
| Tackiness by Handling | Tacky | Slightly tacky |
| Appearance (dry) | Clear | Clear |
| Appearance (in water @ 35° C.) | N/A | Clear |

TABLE 2

| INGREDIENT | CONTROL | EX. 5 | EX. 6 | EX. 7 |
|---|---|---|---|---|
| PBMA | 82.99 | 80.99 | 81.98 | 82.50 |
| PDMS (MW = 800-1400) | — | 2.01 | 1.02 | 0.50 |
| PEG (1000) DMA | 15.01 | 15.00 | 15.00 | 14.99 |
| EGDMA | 0.99 | 1.00 | 1.00 | 1.00 |
| BHMA | 1.00 | 1.01 | 1.01 | 1.01 |
| Tack: Total Energy (mJ) | 1.47 ± 0.34 | 0.31 ± 0.06 | 0.55 ± 0.16 | 1.12 ± 0.35 |
| Appearance (dry) | Clear | Clear | Clear | Clear |
| Stress @ break (mPa) | 4.97 ± 0.48 | 5.29 ± 0.46 | 5.69 ± 0.78 | 5.11 ± 0.43 |
| Strain @ break (%) | 102.4 ± 4.7 | 102.1 ± 5.8 | 107.0 ± 8.3 | 102.0 ± 4.5 |
| Young's Modulus (MPa) | 15.41 ± 0.84 | 12.88 ± 0.88 | 13.60 ± 0.63 | 13.87 ± 0.68 |
| 25% Secant Modulus (mPa) | 5.97 ± 0.25 | 5.65 ± 0.19 | 5.77 ± 0.13 | 5.78 ± 0.13 |
| 100% Secant Modulus (mPa) | 4.84 ± 0.26 | 5.06 ± 0.16 | 5.07 ± 0.28 | 4.96 ± 0.13 |

TABLE 3

| INGREDIENT | EX. 8 | EX. 9 | EX. 10 |
|---|---|---|---|
| PBMA | 83.98 | 79.87 | 77.95 |
| PDMS ($M_n$ 550-700) | 2.01 | 4.09 | 5.94 |
| PEG (1000) DMA | 12.99 | 15.04 | 15.06 |
| EGDMA | 1.02 | 1.00 | 1.05 |
| Appearance (uncured liquid formulation) | Clear | Clear | Clear |
| Appearance (dry) | Clear | Clear | Clear |
| Tackiness by handling | Slightly tacky | Tacky | Tacky |
| Conclusion | Suitable for optical uses | Unsuitable for optical uses | Unsuitable for optical uses |

EXAMPLES 11 AND 12

Monosubstituted polydimethylsiloxane (methylacryloxypropyl-terminated polydimethylsiloxane) ("Monosubstituted PDMS")

The formulations shown below in Table 4 were prepared using the procedure described in Examples 4-7 above. Unlike the dimethylacryloxypropyl-terminated polydimethylsiloxane of the present invention, mono-substituted polydimethylsiloxane did not produce clear, reduced tack materials suitable for use as IOL materials.

TABLE 4

| INGREDIENT | EX. 11 | EX. 12 |
|---|---|---|
| PBMA | 83.97 | 83.87 |
| Monosubstituted PDMS ($M_n$ 800-1200) | — | 2.13 |
| Monosubsituted PDMS ($M_n$ 4K-6K) | 2.02 | — |
| PEG (1000) DMA | 12.99 | 12.98 |
| EGDMA | 1.02 | 1.02 |
| Appearance (uncured liquid formulation) | Cloudy (micellar mixture) | Clear |
| Appearance (dry) | Not cured | Hazy after curing |
| Tackiness by handling | Not applicable | Slightly tacky |
| Conclusion | Unsuitable for optical uses | Unsuitable for optical uses |

We claim:
1. A polymeric ophthalmic or otorhinolaryngological device material comprising
   a) a principal device-forming monomer which is an aryl acrylic hydrophobic monomer of the formula

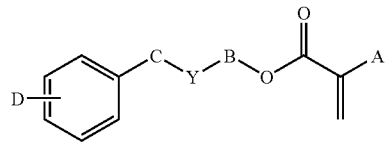

wherein:
A is H, $CH_3$, $CH_2CH_3$, or $CH_2OH$;
B is $(CH_2)m$ or $[O(CH_2)_2]_n$;
C is $(CH_2)_w$;
m is 2-6;
n is 1-10;

Y is nothing, O, S, or NR, provided that if Y is O, S, or NR, then B is $(CH_2)_m$;

R is H, $CH_3$, $C_nH_{2n+1}$ (n=1-10), iso-$OC_3H_7$, $C_6H_5$, or $CH_2C_6H_5$;

w is 0-6, provided that m+w≤8; and

D is H, $C_1$-$C_4$ alkyl, $C_1$-$C_4$ alkoxy, $C_6H_5$, $CH_2C_6H_5$ or halogen, b) a dimethylacryloxypropyl-terminated polydimethylsiloxane macromer in an amount effective to reduce the tack of the polymeric ophthalmic or otorhinolaryngological device material, wherein the dimethylacryloxypropyl-terminated polydimethylsiloxane macromer has the formula

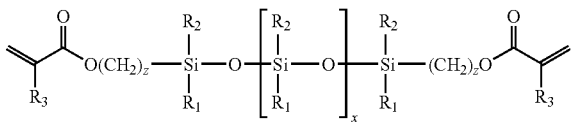

wherein $R_1$ and $R_2$ are independently —$CH_3$, —$CH_2CH_3$, —$CH_2CH_2CH_2CH_3$, $CH_2CH_2CH_2CH_3$, —$C_6H_5$, —$CH_2C_6H_5$, —$CH_2CH_2C_6H_5$, —$CH_2CH_2CH_2C_6H_5$, or —$CH_2CH_2CH_2CH_2C_6H_5$;

$R_3$ is H, $CH_3$, or $CH_2CH_3$;

z is 2-11; and x indicates the number of repeating units and is such that the macromer has a molecular weight of about 300 about 3500; and c) a cross-linking monomer, wherein the principal device-forming monomer is present in an amount of at least about 75% (w/w), wherein the dimethylacryloxypropyl-terminated polydimethylsiloxane macromer is present in an amount from 0.5-3.9% (w/w), wherein the cross-linking monomer is present in an amount of about 0.01-17% (w/w).

2. The polymeric ophthalmic or otorhinolaryngological device material of claim 1 wherein A is $CH_3$, B is $(CH_2)_m$, m is 2-5, Y is nothing or O, w is 0-1, and D is H.

3. The polymeric ophthalmic or otorhinolaryngological device material of claim 2 wherein the aryl acrylic hydrophobic monomer is selected from the group consisting of 4-phenylbutyl methacrylate; 5-phenylpentyl methacrylate; 2-benzyloxyethyl methacrylate; and 3-benzyloxypropyl methacrylate.

4. The polymeric ophthalmic or otorhinolaryngological device material of claim 1 further comprising one or more components selected from the group consisting of reactive UV absorbers and reactive blue-light absorbers.

5. The polymeric ophthalmic or otorhinolaryngological device material of claim 1 wherein the dimethylacryloxypropyl-terminated polydimethylsiloxane macromer is present in an amount from 0.5-2% (w/w).

6. The polymeric ophthalmic or otorhinolaryngological device material of claim 1 wherein the dimethylacryloxypropyl-terminated polydimethylsiloxane macromer is present in an amount from 0.8-1.2% (w/w).

7. The polymeric ophthalmic or otorhinolaryngological device material of claim 1 wherein $R_1$=$R_2$=$CH_3$; $R_3$ is H, $CH_3$, or $CH_2CH_3$; z=3; and x=0-22.

8. The polymeric ophthalmic or otorhinolaryngological device material of claim 1 wherein x =5-14.

9. The polymeric ophthalmic or otorhinolaryngological device material of claim 1 wherein x=2-5.

10. The polymeric ophthalmic or otorhinolaryngological device material of claim 1 wherein the material is an ophthalmic device material and has a refractive index of at least 1.50.

11. The polymeric ophthalmic or otorhinolaryngological device material of claim 1 wherein the material has a Tg less than about +15° C.

12. The polymeric ophthalmic or otorhinolaryngological device material of claim 1 wherein the material has an elongation of at least 90%.

13. The polymeric ophthalmic or otorhinolaryngological device material of claim 1 wherein the cross-linking component comprises one or more cross-linking agents selected from the group consisting of ethylene glycol dimethacrylate; diethylene glycol dimethacrylate; allyl methacrylate; 1,3-propanediol dimethacrylate; 2,3-propanediol dimethacrylate; 1,6-hexanediol dimethacrylate; 1,4-butanediol dimethacrylate; $CH_2$=$C(CH_3)C$(=O)O—$(CH_2CH_2O)_p$—$C$(=O)$C(CH_3)$=$CH_2$ where p=1-50; $CH_2$=$C(CH_3)C$(=O)$O(CH_2)_tOC$(=O)$C(CH_3)$=$CH_2$ where t=3-20; and their corresponding acrylates.

14. The polymeric ophthalmic or otorhinolaryngological device material of claim 1 wherein the principal device-forming monomer is present in an amount of at least about 80% (w/w).

15. The polymeric ophthalmic or otorhinolaryngological device material of claim 1 wherein the aryl acrylic hydrophobic monomer is selected from the group consisting of 4-phenylbutyl methacrylate; 5-phenylpentyl methacrylate; 2-benzyloxyethyl methacrylate; and 3-benzyloxypropyl methacrylate; and the cross-linking monomer is $CH_2$=$C(CH_3)C$(=O)O—$(CH_2CH_2O)_p$—$C$(=O)$C(CH_3)$=$CH_2$, where p is such that the number average molecular weight of the cross-linking monomer is about 1000.

16. An intraocular lens optic comprising the polymeric device material of claim 1

17. A device comprising the device material of claim 1 wherein the device is selected from the group consisting of a contact lens; a keratoprosthesis, a corneal inlay or ring; an otological ventilation tube; and a nasal implant.

* * * * *